United States Patent

Makinen

[11] Patent Number: 5,199,941
[45] Date of Patent: Apr. 6, 1993

[54] CONTOURED ANKLE BRACE AND STABILIZER

[76] Inventor: Robbie W. Makinen, 15601 E. 43rd Ter., Independence, Mo. 64055

[21] Appl. No.: 850,501

[22] Filed: Mar. 13, 1992

[51] Int. Cl.$^5$ ............................................. A61F 5/04
[52] U.S. Cl. ........................................ 602/27; 602/23; 602/6
[58] Field of Search ............... 602/5, 6, 23, 27–29, 602/62, 65; 128/882

[56] References Cited

U.S. PATENT DOCUMENTS

| | | |
|---|---|---|
| 1,089,305 | 3/1914 | Baughman ............... 602/23 |
| 3,643,656 | 2/1972 | Young et al. . |
| 3,800,789 | 4/1974 | Schloss . |
| 3,943,923 | 3/1976 | Scheinberg . |
| 3,955,565 | 5/1976 | Johnson, Jr. . |
| 4,133,311 | 1/1979 | Karczewski . |
| 4,280,489 | 7/1981 | Johnson, Jr. . |
| 4,414,965 | 11/1983 | Mauldin et al. ............ 602/23 |
| 4,494,534 | 1/1985 | Hutson ........................ 602/23 X |
| 4,590,932 | 5/1986 | Wilkerson ................... 602/65 |
| 4,628,945 | 12/1986 | Johnson, Jr. . |
| 4,641,639 | 2/1987 | Padilla ........................ 602/23 |
| 4,688,559 | 8/1987 | Vito et al. ................... 602/23 |
| 4,729,370 | 3/1988 | Kallassy .................... 602/65 |
| 4,844,094 | 7/1989 | Grim . |
| 4,966,134 | 10/1990 | Brewer . |
| 5,000,195 | 3/1991 | Neal ............................ 602/27 |
| 5,007,416 | 4/1991 | Burns et al. ................ 602/27 |
| 5,014,691 | 5/1991 | Cueman et al. ............. 602/27 |
| 5,022,390 | 6/1991 | Whiteside ................... 602/23 X |

Primary Examiner—Richard J. Apley
Assistant Examiner—Linda C. M. Dvorak
Attorney, Agent, or Firm—Harry A. Pacini

[57] ABSTRACT

In an orthopedic device as a flexible contoured ankle stabilizer having a generally U-shaped "stirrup" member having a base portion and a pair of removably attachable opposed contoured vertical shells with a compressible medium disposed interiorly of the opposed contoured shells, the improvement wherein each of the opposed contoured shells has a heel bone extension protruding generally along and toward the back of the ankle in the vicinity of the heel; wrapping straps used to hold the contoured shells with heel extensions and attached stirrup base in place on the ankle and heel.

8 Claims, 7 Drawing Sheets

CONTOURED ANKLE BRACE AND STABILIZER

The present invention relates generally to an orthopedic device and more particularly to an ankle stabilizer designed to stabilize movement of the calcaneus (heel bone) and talus bones of the ankle (called the sub-talor joint), as well as the tibia, fibula and talus (called the ankle joint), which when put together stabilize the entire ankle. The device relates to a contoured ankle brace for wearing on a human ankle which can be worn with footwear.

BACKGROUND AND DISCUSSION OF PRIOR ART

The calcaneus and talus bone which make up the sub-talor joint of the ankle, bear the entire body weight. This sub-talor joint, as well as the tibia, fibula and talus joint line combine with strong ligaments to make up the ankle's principle means for joint stability. The tibia and fibula end distally in two easily felt prominences called the malleoli on either side of the ankle. The talus resembles a saddle that the distal tibia and fibula rest on and move over. There are four major ligaments that attached to these bones of the ankle. On the medial side (inside) there are the deltoid ligaments. On the lateral side (outside) there are the calcaneo-fibular ligament, the anterior talo-fibular ligament and the posterior talo-fibular ligament. All of these major ligaments attach either to the calcaneus or talus bones.

In considering the causation of skeletal abnormalities and ankle sprains, it must be remembered that the calcaneus and talus are the weight-bearing bones in the ankle. If the heel is turned in, body weight is shifted to the outside and a stretch is placed on the lateral ligaments. If the heel is turned out, force is placed on the medial ligaments. Therefore, it is the stability of the calcaneus that controls the stability of the ankle joint. Similarly, any structural foot or leg deformity which causes the calcaneus to shift from its vertical position will favor ankle sprains.

The prior art ankle brace described in Johnson, Jr., U.S. Pat. No. 4,280,489 relates to an orthopedic apparatus for use in connection with the lower extremity and for immobilizing the ankle against inversion or eversion while permitting planer-flexion and dorsi-flexion. Grim, U.S. Pat. No. 4,844,094 and Brewer, U.S. Pat. No. 4,966,134, both disclose a U-shaped stirrup having a base portion and a pair of opposed sidewalls shells similar to that of Johnson, Jr. ('489).

In all three of the aforementioned patents, the pair of opposed sidewall shells follow the line of the tibia and fibula past the malleoli and then become narrower the closer they get to the bottom of the leg and foot, leaving the calcaneus exposed. This in turn leaves the sub-talor joint unprotected. If the sub-talor joint and the calcaneus are not stabilized, then a sprain involving the calcaneo-fibular ligament or the deltoid ligament cannot heal correctly. The deltoid also attaches to the calcaneus, or in the case of preventative use, the arrangement would be similar to wearing no brace at all.

Each of U.S. Pat. Nos. 4,280,489, 4,844,094 and 4,966,134 relate to an ankle brace or protector to limit inversion and eversion, with the only apparent difference between the apparatus described being what is interiorly disposed therein (i.e., air, gel, a pad with higher surface friction space, or the like). These references disclose ankle orthoses each of which simply act as a splint, somewhat limiting inversion and eversion, but falling far short of real total ankle stability. No attempt is made in the prior art references to control the sub-talor joint which includes the calcaneus. Without controlling the calcaneus and sub-talor joint and their ligaments, ankle braces described in the prior art are cannot provide the ankle stability obtained with the present invention.

Most of the major ligaments in the ankle attach to the calcaneus at some point. With this attachment in mind and the fact that the total body weight is placed on the heel bone, when the ankle inverts or everts, this does not result in inversion or eversion, which the prior art is trying to limit. However, the prior art does not anticipate rear foot valgus or varus stress. It is critical that an ankle brace control the calcaneus as well as the tibia, fibula and talus. A need therefore exists for a complete ankle orthosis which not only limits standard inversion and eversion, but stabilizes rear foot stresses by immobilizing the calcaneus. This is a principle object of the present invention.

It is realized by the present invention that ankle stability is gained not just by limiting inversion and eversion, but by reducing all abnormal torques in the ankle that may be twisting or pulling the foot toward a potential sprain. While planar-flexion and dorsi-flexion are critical to a normal range of motion (walker, running, etc.), anterior excursion and some posterior excursion at the joint line must also be limited to provide yet more stability. Excursion occurs when the talus glides forward or backward at the joint, due to ligament lesions, principally the anterior talo-fibular ligament.

A biomechanical workup is considered in determining the cause of frequent sprains to the ankle. The deforming force must be neutralized with the use of orthotic devices with a rearfoot post to properly balance the foot. In this way the chance of future sprains should be reduced. Ankles with extremely flexible and elastic joints also have a tendency toward ankle sprain. Once an ankle is sprained, it is never as strong as before the injury. Therefore, the use of an orthotic device for the prevention of future recurrent ankle sprains is most necessary in an active ankle.

A rigid orthosis is necessary to prevent the heel from eversion. An orthotic device that grasps the heel bone and, with the addition of a rear platform or post, only allows the heel to move an amount necessary for normal function also is desired.

SUMMARY OF THE INVENTION

It is the foremost object of the present invention to overcome the deficiencies of the prior art and to provide a reusable ankle stabilizer that limits not only inversion and eversion, but all abnormal movements at the ankle joint and the sub-talor joint, by controlling and stabilizing the calcaneus (heel bone), which will in turn control the whole ankle.

Therefore, it is a further object of the present invention to provide for superior stability at both of the joint lines by controlling movement of the calcaneus, as well as the tibia, fibula, talus and all the major ligaments.

Yet a further object of this invention is to provide an ankle stabilizer which may be comfortably worn inside a conventional shoe, and limit all abnormal movements of the ankle, such as subluxation, anterior and posterior excursion.

Another object of this invention is to provide an ankle stabilizing apparatus for the stability needed to neutralize any deformities at both joint lines associated with the prevention of healing of ankle sprains.

Yet another object of this invention is to provide a reusable ankle stabilizer having a compressible liner and means for securely and firmly attaching and readjusting said stabilizer to the ankle.

These and additional objects of the present invention may be achieved, as briefly described, by an orthotic device with two opposed, anatomically contoured shells which start on the distal fibula and tibia (above the malleoli), run parallel to the fibula and tibia until just below the medial and lateral malleoli at such time the shells widen posteriorly (back) to encase the calcaneus (heel bone) on both the medial and lateral sides, that is, the opposed flexible contoured shells each have a heel bone extension protruding generally toward the back of the ankle in the vicinity of the heel. Two distal, elasticized straps then start on each shell over the malleoli and travel under the foot and over the heel bone, thereby locking in the heel bone and both joint lines, and connecting back to each other. For comfort, foam or a compression medium is disposed interiorly of the opposed anatomically contoured shells. Said contoured shells each contain slots. Two slots, distal and horizontal, are used to accept U-shaped thin plastic members which go under the foot and connect the two shells. There are two proximal slots on the medial shell to accept the top two VELCRO ® type straps that fasten the stabilizer to the tibia and fibula. The wrapped straps hold the contoured shells and heel extensions in secured placement.

DESCRIPTION OF THE DRAWINGS

The foregoing and still further features and advantages of the present invention, as well as a more complete understanding of the same, will be made apparent from a study of the following detailed description of the present invention in connection with the accompanying drawings wherein:

FIG. 3 shows the straps and shells in place, the entire bone structure and all the ankle ligaments of the ankle which are controlled and stabilized. A more detailed description of the application of said straps is shown in FIGS. 12-15.

FIGS. 6A, 6B, 6C, and 6D show the medial shell outlines of the present invention, '489, '094 and '134. This figure shows that all of the prior art devices will limit inversion and eversion; however, only the present invention with the posterior extensions limits calcaneus valgus and varus rolling as well. When the straps of FIG. 3 are in place, the calcaneus is locked into a fixed position and anterior and posterior shifts of the joint lines are removed. With all abnormal movements of the entire ankle restricted, the ankle is far more stable than with the "splint" braces as described in '489.

FIG. 7 shows how both shells of each invention would conform to the medial and lateral sides of the right ankle. In '489, '094 and '134, both the medial and lateral shells are almost identical. In the present invention it is taken into consideration that the medial and lateral sides of the ankle are not identical. Thus the present invention is more anatomically correct than the prior art apparatus, with the inward shaped contour on the lower portion of the lateral shell.

FIGS. 10 and 11 show how the bottom plastic base platform 16 is attached to the shell with standard hook and loop type fasteners, and how the top two straps 13, 13a connect the medial and lateral shells 10, 11 to each other and the ankle at the proximal end of the apparatus.

FIGS. 12-15 show how the bottom two elasticized straps 15, 15a (one starting over the lateral malleoli, and one starting over the medial malleoli) compress the bottom half of the medial and lateral (medial side shown) shells and lock in the calcaneus, ankle joint, sub-talor joint, and thus all the ligaments of the ankle as shown in FIG. 2. The straps end connecting to each other by means of standard hook and loop type fasteners.

Figure 1:
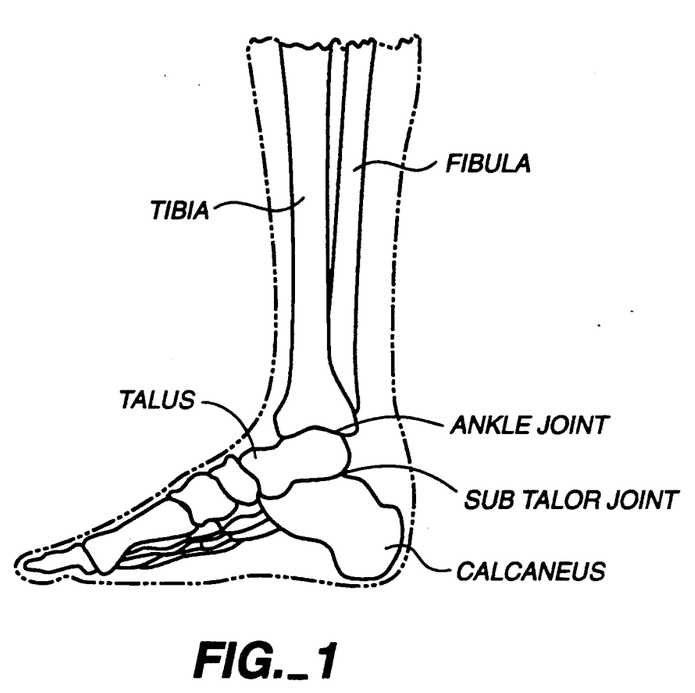
FIG. 1 shows the bone structure of the medial side of the right lower extremity, and the bones and joints associated with the ankle.
Figure 2:
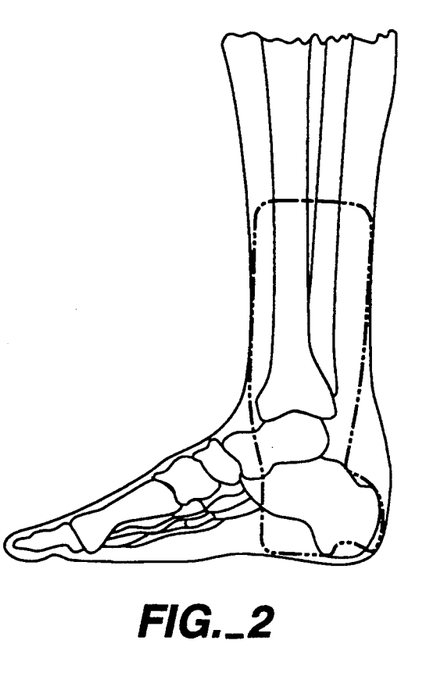
FIG. 2 is a medial skeletal view of the right lower extremity, with the outline of the medial shell (lateral shell, the same) of the present invention. This figure shows how the shell covers the ankle joint, sub-talor joint, and entire calcaneus, thus, the entire ankle.
Figure 3:
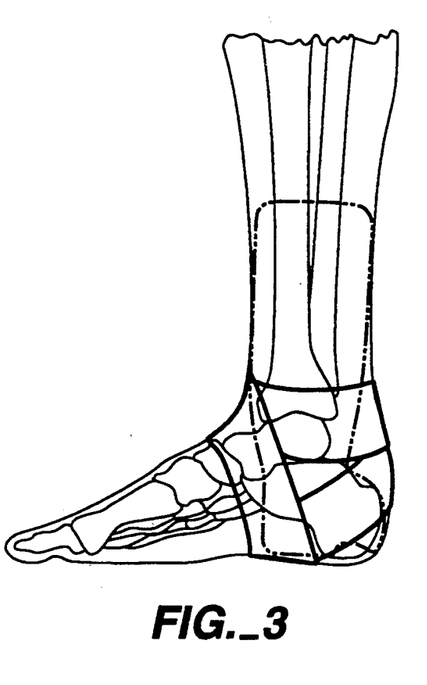
FIG. 3 is a medial skeletal view of the right lower extremity with the outline of the medial shell, with the elasticized hook and loop (VELCRO ®) straps of the present invention, in place.
Figure 4:
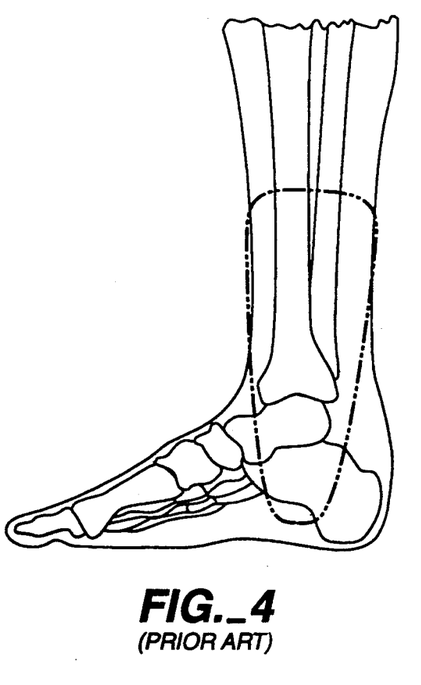
FIG. 4 shows a medial skeletal view of the right lower extremity with the outline of the medial shell (lateral side of the same) of the prior art '489 apparatus. This figure shows that while the prior art apparatus is an adequate splint for limiting inversion and eversion, no stability is given to the calcaneus, thus, no real stability is given to the entire ankle, and no abnormal movements of the joint lines and ligaments are prevented other than inversion and eversion. The shell outline is almost identical for '094.
Figure 5:
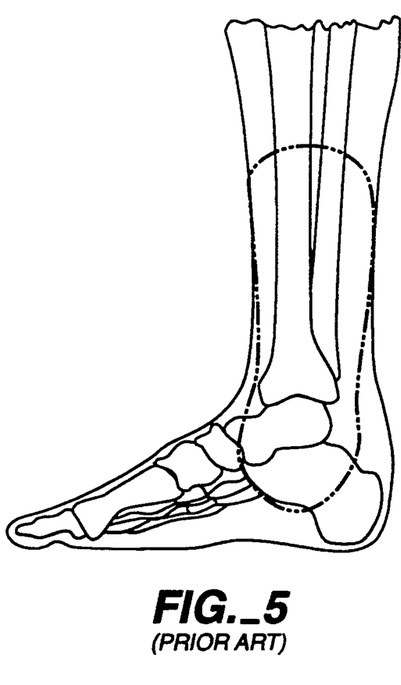
FIG. 5 is a medial skeletal view of the right lower extremity with the outline of the medial shell of the invention in '134 producing the same results as discussed in regard to FIG. 4, above.
Figure 6A:
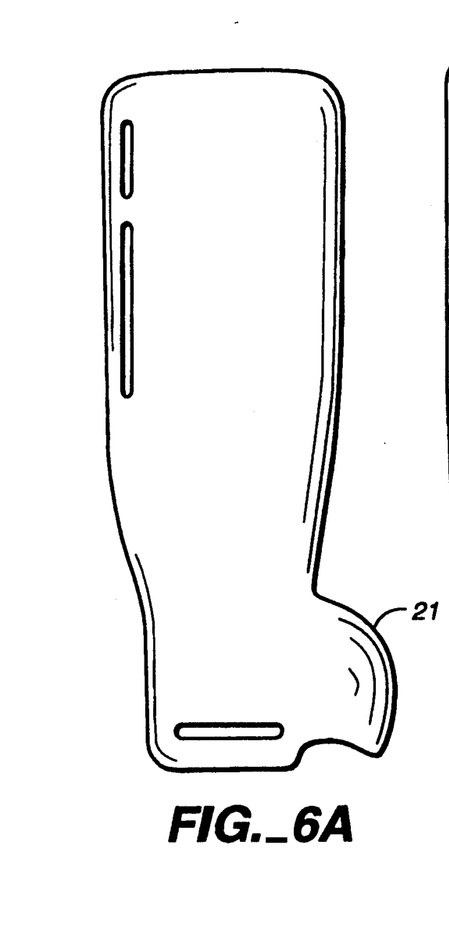
Figure 6B:
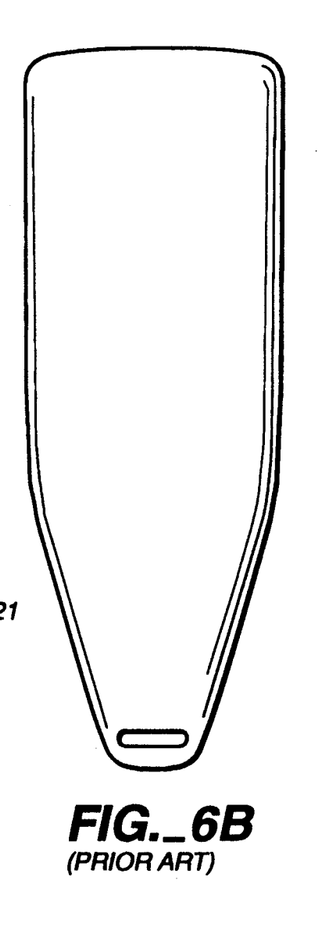
Figure 6C:
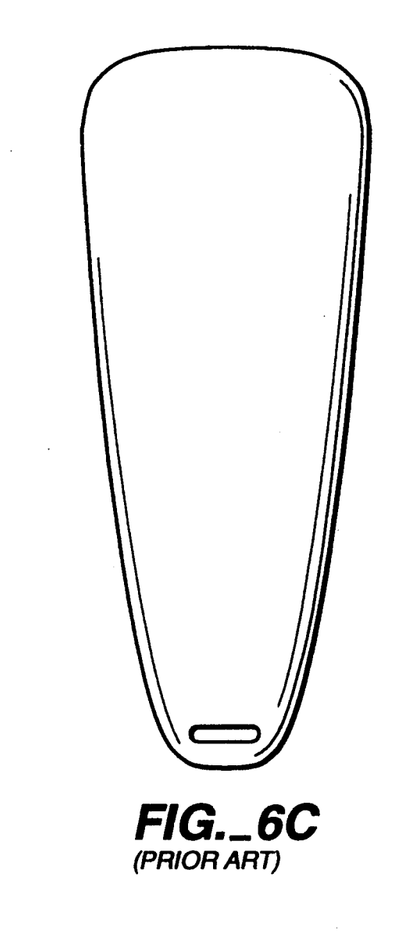
Figure 6D:
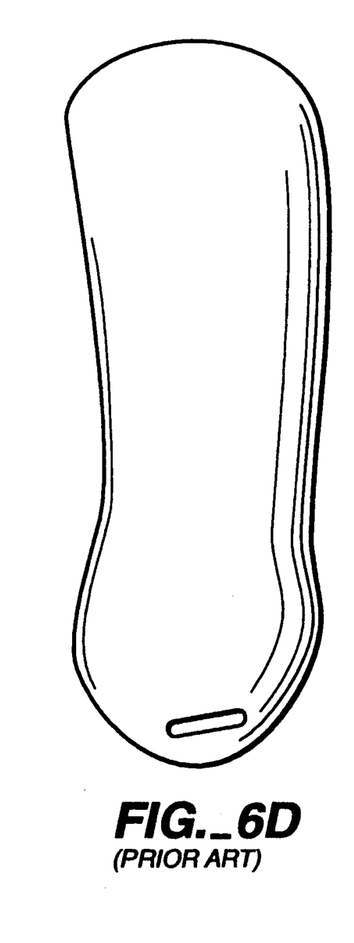
Figure 7A:
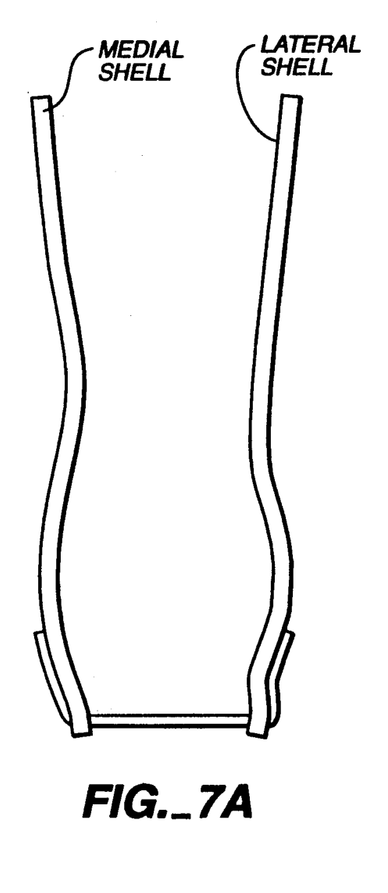
FIGS. 7A, 7B, 7C, and 7D show an anterior (front) view of the present invention, each prior art reference, '489, '094 and '134.
Figure 7B:
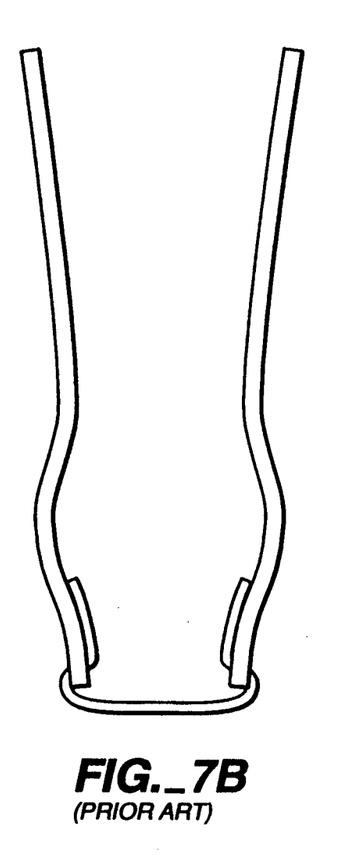
Figure 7C:
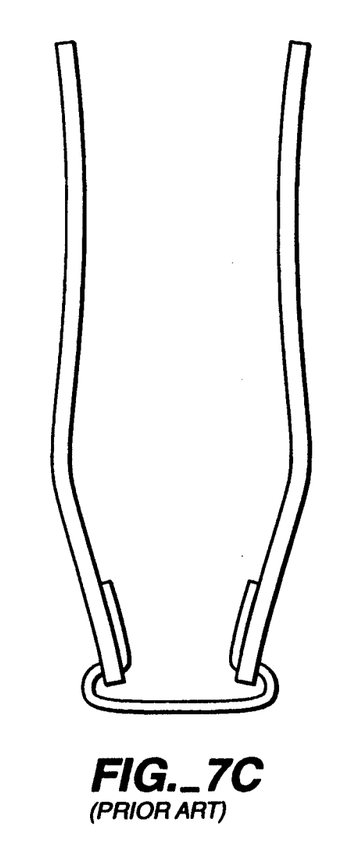
Figure 7D:
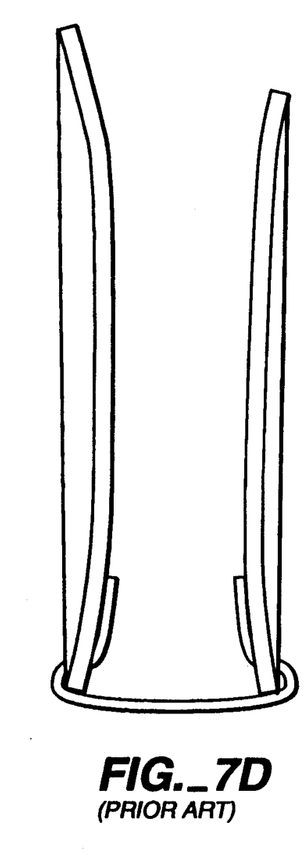
Figure 8:
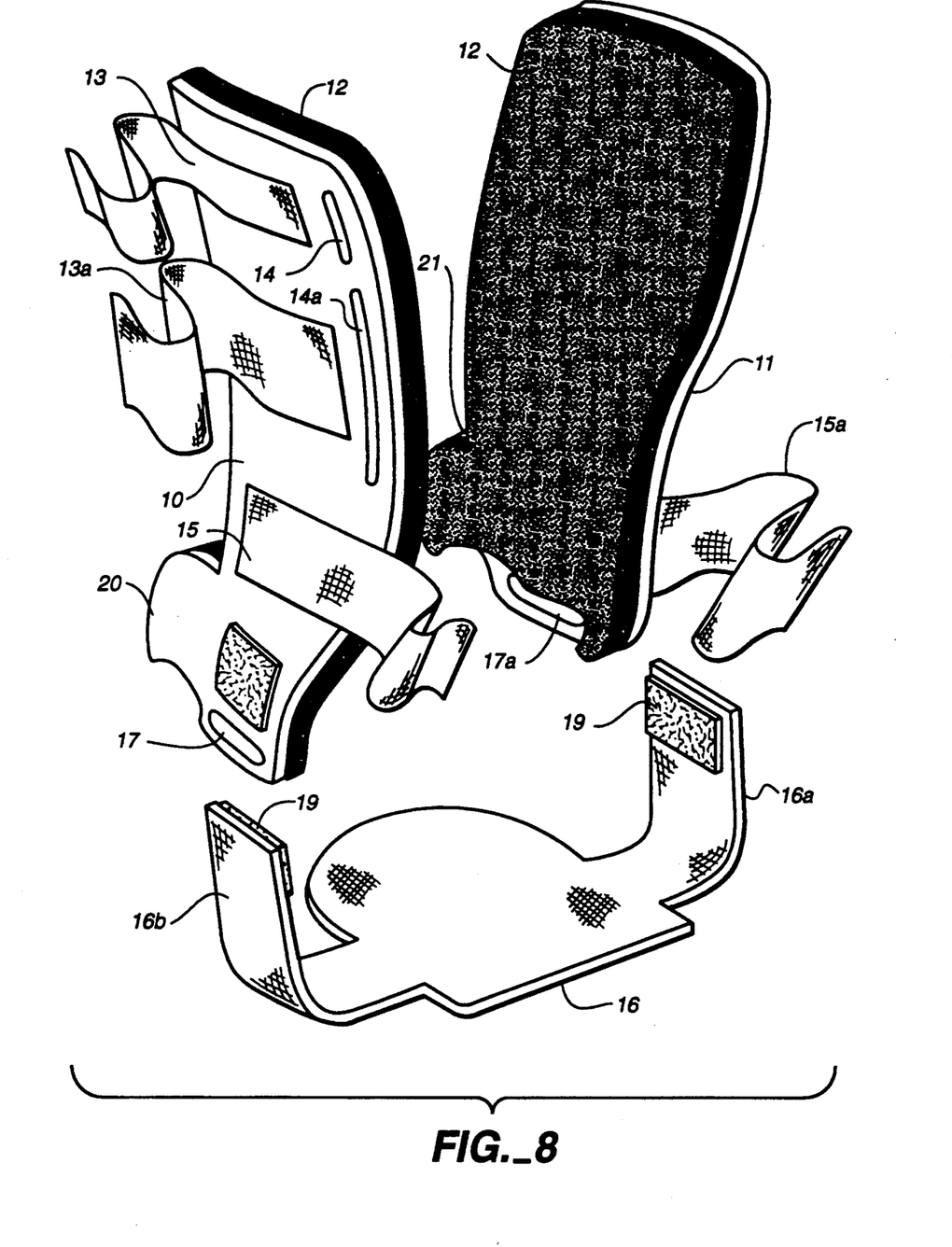
FIG. 8 is an exploded perspective view of the present invention complete with all the straps, ¼" foam liner, and bottom plastic platform to connect the medial and lateral shells together.
Figure 9:
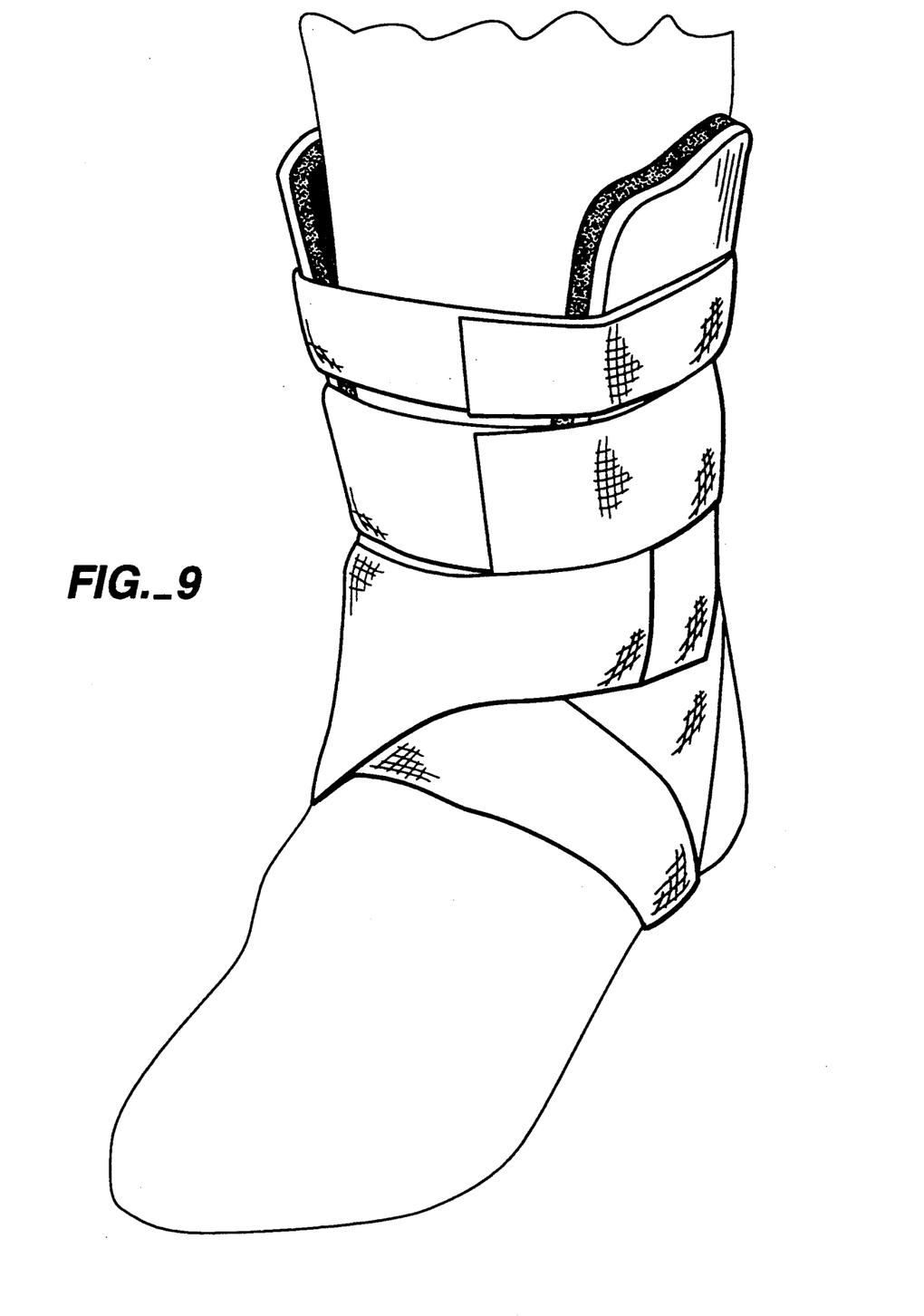
FIG. 9, a perspective view of the present invention in place on the ankle. One can see by FIG. 8 that when the present invention is in place on the ankle, the ankle is surrounded and secured so that all abnormal movements are restricted.
Figure 10:
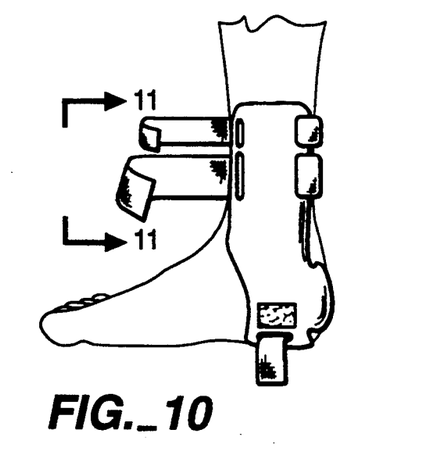
FIGS. 10-15, inclusive represent detailed diagrammatic showing the preferred wrap sequence of the heel lock securing the strap.
Figure 11:
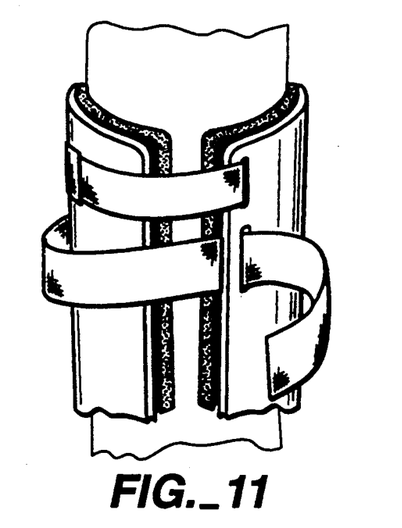

The medial shell 10 and the lateral shell 11 are preferably injection molded polyethylene plastic parts that are formed to duplicate the contours of the medial and lateral sides of the ankle. The preferably ¼" closed cell foam 12 being interiorly disposed therein is cut to match the outline of the medial and lateral shells. Two preferably VELCRO ® type straps; one 1" wide 13 and one 2" wide 13a, each starting on the media shell 10, encircling the distal tibia, fibula, and lateral shell 11, then traveling through two vertical slots 14, 14a at the proximal end of the media shell 10 and traveling back the opposite way and hooking back on themselves [FIG. 9 and FIG. 10], said straps enabling the proximal ends of the apparatus to be tightened securely. The complete apparatus of FIG. 7 and FIG. 8 consists of two, preferably elasticized 2" wide, straps; one strap 15 starting on the medial shell over the medial malleoli and one strap 15a starting on the lateral shell over the lateral malleoli. When said straps are wrapped according to the preferred configuration of FIG. 8 and FIG. 9, the medial shell 10 and the lateral shell 11 compress against the bottom half of the medial and lateral sides of the ankle, thereby locking the bones of the ankle joint, sub-talor joint, and most importantly, the entire calcaneus, into a normal fixed position as shown in FIG. 3 and FIG. 9.

Figure 12:
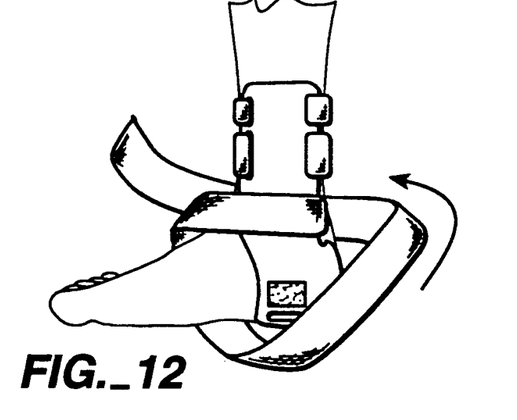
Figure 13:
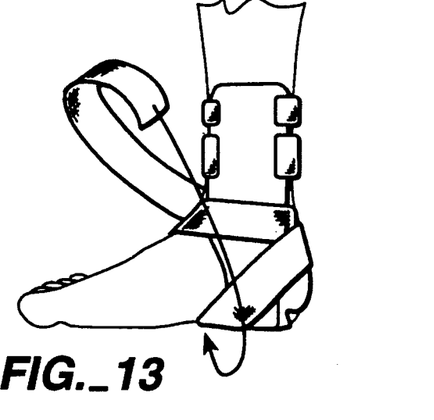
Figure 14:
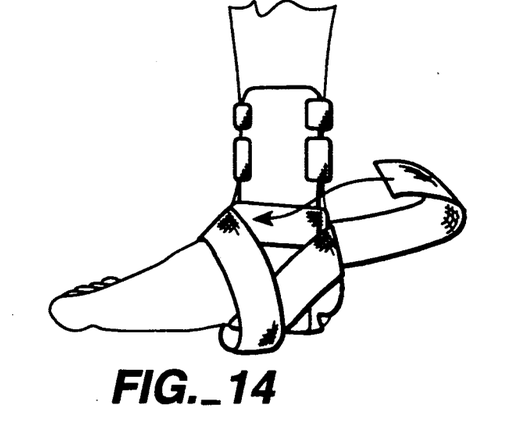
Figure 15:
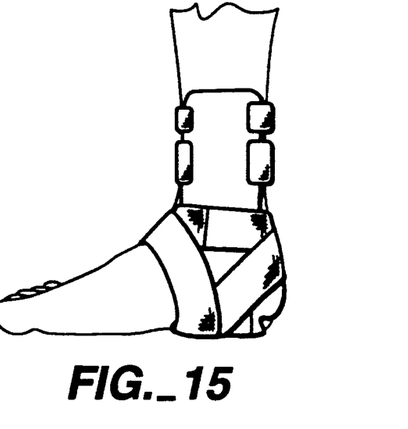

The first strap 15 starts in FIG. 12 on the distal end of the medical shell, travels laterally over the top of the foot, down over the bottom anterior portion of the lateral shell, under the base portion of the apparatus. Said strap then starts back up the bottom posterior portion of the medial shell (running diagonally beside the calcaneus) then runs across the back of the ankle and connects (with a VELCRO ® type hook and loop) to the beginning of the second strap 15a. With reference to FIG. 13, the second strap 15a starts on the distal end of the lateral shell, travels medially over the top of the foot, down over the bottom anterior portion of the medial shell, under the base portion of the apparatus. Said second strap then starts back up the bottom posterior portion of the later shell FIG. 14 (running diagonally beside the calcaneus) then runs across the back of the ankle and connects (with a VELCRO ® type hook and loop fastener) to the beginning of said first strap FIG. 15. Other fastening means are contemplated, however the VELCRO ® type hook and loop allow conform and ease of adjustment.

Associated with the medial and lateral shells, there is a base platform member 16 with a pair of oppositely extending attaching portions 16a and 16b formed from a common piece of thin plastic, preferably polyethylene. The plastic is cut to size and shaped substantially as shown to conform and travel under the calcaneus and connecting (with fasteners or a layer of fastening material such as that commonly sold under the name VELCRO ®) the medial and lateral shells at the most distal portion of the apparatus. As seen in FIG. 8 the mating VELCRO ® type hook and loop fastener patch elements 18 ad 19 connect the base platform to the medial and lateral shells at the most distal end of the apparatus. Horizontal slots 17 and 17a at the most distal ends of the medial and lateral shells 10 and 11, respectively, are used to guide and hold the attaching portion of the base platform.

At the lower portion of each contoured shell member for cooperation with the securing heel securing straps are rearwardly protruding extension known as shell heel extensions 20 and 21, or rear foot extension. Said shell heel extensions 20 and 21 lie along side the calcaneus of the inner and outer portion of the heel in the rear foot region. The shell heel extensions when combined with the wrapped heel lock securing strap provide a superior degree of stability, support and alignment to the ankle and foot. Thereby, such rear foot post extensions together with the stirrup or base member 15 there is provided superior support and secured alignment to the ankle and foot. Normal walking or running movements of the ankle and foot are not hindered by this preferred arrangement. Therefore by using a multiplicity of straps, effective immobilization and conformity to the ankle joint and heel locking can be achieved. Also a maximum degree of adjustment for comfort and maintenance of adequate blood supply to the joint as may be required under the circumstances, if swelling is present.

Other modifications, alterations and variations of the present invention may occur to those with ordinary skill in the art to which this invention pertains. Without departing from the scope and spirit of the appended claims such changes, modifications, equivalents and alterations will be evident. Accordingly, the present invention should be limited only by the scope of the appended claims, and those skilled in the art will appreciate that the invention can be embodied in forms other than those herein disclosed for purposes of illustration.

What is claimed is:

1. An anatomically contoured apparatus for use in connection with a human lower extremity to obtain calcaneus stability and protection of the sub-talor joint for total ankle stability comprising: medial and lateral molded plastic shells sized and configured for placement on the medial and lateral sides of the ankle, respectively, said shells adapted to cover the distal tibia and distal fibula, and extending down over the malleoli then widening posteriorly into a rearward heel extension to thereby encompass the entire calcaneus, sub-talor joint, the talus, distal tibia and distal fibula and all ligaments therein, and means for holding said shells in ankle stabilizing conformation, wherein said shells are used in conjunction with each other to prevent anterior and posterior excursion, joint line shifts, and calcaneus valgus and varus stresses.

2. The apparatus of claim 1 wherein said means for holding are two elasticized straps, one starting on the medial shell and one starting on the lateral shell wrapped across around said lower extremity whereby said shells compress against the ankle, thereby locking the bones of the ankle joint, sub-talor joint, and the entire calcaneus into a normal fixed position.

3. The apparatus of claim 1 wherein said means for holding said medial and lateral shells at the distal tibia and fibula are two hook and loop straps, and whereby each strap starts on the medial shell, encircles the distal tibia, fibula, and lateral shell; then travels through two vertical slots at the proximal end of the medial shell and travels back the opposite way, hooking back onto themselves.

4. A contoured ankle brace and stabilizer comprising:
  (a) a pair of flexible molded vertical opposing side contoured support shells for placement on opposing sides of an ankle and attachment to the lower leg, said shells each having an upper end and a lower end, said lower end including a heel bone extension protruding rearwardly toward the back of the heel for protection of the sub-talor joint and calcaneus stability;
  (b) means for removably and adjustably securing said support shells and for securing the heel bone extensions in place on the heel bone and lower leg;
  (c) a heel platform adjustably connected to said support shells; and
  (d) said molded support shells having an inner liner coextensive therewith.

5. The brace and stabilizer of claim 4 in which said support shells are a thin lightweight plastic material.

6. The brace and stabilizer of claim 5 in which said plastic material is reinforced with glass fibers.

7. The method of protecting the sub-talor joint and obtaining calcaneus stability comprising:
  (a) applying to a human lower extremity paired molded plastic medial and lateral shells having rearwardly extending shell heel extensions at the lower end thereof; and
  (b) adjustably securing said shells about the distal tibia and fibula, wherein said shells are used in conjunction with each other to prevent anterior and posterior excursion, joint line shifts and calcaneus valgus and varus stresses.

8. The improved orthopedic device for use on the lower human extremity in the ankle region, having a base portion, a pair of spaced apart contoured molded plastic medial and lateral shells and means for securing, the improvement comprising attached to the lower portion of each of said spaced apart molded plastic medial and lateral shells a heel bone extension protruding generally along and toward the back of the ankle and adapted to cover the heel.

* * * * *